(12) United States Patent
Gilmer et al.

(10) Patent No.: US 7,486,993 B2
(45) Date of Patent: Feb. 3, 2009

(54) BRAIN STIMULATION METHOD AND DEVICE

(75) Inventors: James Ray Gilmer, Garland, TX (US); John G. Buie, Waxahachie, TX (US); John R. Buie, Terrell, TX (US); Jason Worchel, Honoka'a, HI (US)

(73) Assignee: Neurotone Systems, Inc., Garland, TX (US)

( * ) Notice: Subject to any disclaimer, the term of this patent is extended or adjusted under 35 U.S.C. 154(b) by 240 days.

(21) Appl. No.: 10/912,630

(22) Filed: Aug. 5, 2004

(65) Prior Publication Data

US 2006/0030897 A1 Feb. 9, 2006

(51) Int. Cl.
*A61N 1/372* (2006.01)

(52) U.S. Cl. .............................. 607/72; 600/544; 607/45

(58) Field of Classification Search ................. 600/382, 600/383, 544; 607/2, 72, 115
See application file for complete search history.

(56) References Cited

U.S. PATENT DOCUMENTS

| 768,721 | A | | 8/1904 | Bassell |
| 3,388,699 | A | | 6/1968 | Webb et al. |
| 3,620,219 | A | | 11/1971 | Barker |
| 3,659,614 | A | | 5/1972 | Jankelson |
| 3,718,132 | A | * | 2/1973 | Holt et al. ................... 600/26 |
| 4,226,246 | A | | 10/1980 | Fragnet |
| 4,907,601 | A | * | 3/1990 | Frick ........................... 607/72 |
| 4,979,508 | A | | 12/1990 | Beck |
| 5,038,780 | A | * | 8/1991 | Boetzkes ...................... 607/50 |
| 6,016,449 | A | | 1/2000 | Fischell et al. |
| 6,041,262 | A | | 3/2000 | Beder |
| 6,591,138 | B1 | | 7/2003 | Fischell et al. |
| 6,641,562 | B1 | * | 11/2003 | Peterson ...................... 604/141 |
| 6,708,064 | B2 | * | 3/2004 | Rezai ........................... 607/45 |
| 7,026,927 | B2 | * | 4/2006 | Wright et al. ........... 340/539.12 |
| 2003/0018366 | A1 | | 1/2003 | Lamont |
| 2003/0097161 | A1 | | 5/2003 | Firlik et al. |
| 2004/0088024 | A1 | | 5/2004 | Firlik et al. |

OTHER PUBLICATIONS

Ferdjallah, Mohammed, Acquisition and Analysis of Electroencephalographic Activity (EEG) in the Presence of Noise With Application to Cranial Electrotherapy Stimulation (CES), Dec. 1994, The University of Texas at Austin.

* cited by examiner

*Primary Examiner*—Carl H Layno
*Assistant Examiner*—Frances P Oropeza
(74) *Attorney, Agent, or Firm*—Carr LLP

(57) ABSTRACT

The present invention provides for applying electric impulse trains to a patient. A ditherer generates a plurality of indicia, each of the plurality of indicia corresponding to an impulse train. The ditherer is further configured to vary the time period between generating the indicia corresponding to the plurality of impulse trains. There is also a plurality of outputs for each of the plurality of indicia. Each of the two impulse trains are substantially 180 degrees out of phase with one another.

29 Claims, 4 Drawing Sheets

DITHER/ PERIOD OSCILLATOR
440

PLACEBO ON/OFF SWITCH
430

BATTERY SAVE CIRCUIT / POWER OFF TIMER
420

WAVEFORM GENERATOR
400

*FIG. 4*

BRAIN STIMULATION METHOD AND DEVICE

FIELD OF THE INVENTION

The present invention is generally directed to brain stimulation and, more particularly, to dithered electrical impulses applied to the brain or other parts of the body.

BACKGROUND

Cranial Electrotherapy Stimulation (CES) is a therapeutic technique used in the treatment of various neurological disorders. Generally, CES involves the application of microelectric pulses to the patient via electrodes placed on the head. CES works to bring the neurotransmitters back into normal pre-stress homeostasis. CES will enable the patient to begin from a "fresh start" position biochemically.

In other words, the neurotransmitters in the brain are ideally in a homeostatic balance with each other, so that if any group of neurons produce too much of a given neurotransmitter, another counteracting group of neurons will fire a counteracting neurotransmitter to inhibit the firing of the first neuron group. The counteracting neurotransmitter diminishes the production of the initial, given neurotransmitter by the first group of neurons. In this way, acetylcholine and dopamine maintain a mutual balance; endorphins and norepinephrine maintain a mutual balance, and so forth.

However, if a real or perceived stressor arises, the brain quickly shifts out of the normal homeostasis to prepare the person for fight or flight. When the emergency subsides, the brain comes back to its original balance and the person returns to normal. If the stressor continues and does not subside over time, the brain does not return to normal homeostasis, but sets up a new homeostasis based on its stress condition. Bad things happen to the body and brain when the stress homeostasis is set up, with the resulting cortisol attacking everything from the memory centers in the brain to bodily organs such as the heart and stomach.

Scientific literature supports that CES gains its treatment benefit by stimulating the brain tissue to manufacture the various neurotransmitters. The numerous stresses that impinge upon a person tend to shift the body's hormone structure to adjust to the continuing presence of the stressor. This adjustment creates a biochemical imbalance that can be very destructive to the body and brain. As part of the stress reaction, the neurotransmitters in the brain are shifted out of normal states and into altered states of balance.

One role of CES is to force the neurotransmitters out of the stress homeostasis and back into their original, pre-stress balance. It does this by stimulating the various sections of the brain to manufacture neurotransmitters. If the neurons that manufacture norepinephrine have been working overtime (due to the stress reaction) while those making endorphins have remained relatively quiescent, when CES is applied, over the passage of time the norepinephrin neurons will be activated relatively less. The endorphin neurons will then be relatively more active than they were, and at their new strength will begin inhibitory firing of the norepinephrine neurons. The treatment process will ultimately bring them into similar firing rates in which they once again maintain a mutual, homeostatic balance.

However, there are problems associated with conventional CES. For instance, people have varying degrees of responsiveness to CES. Furthermore, monitoring the varying degrees of responsiveness can be of concern.

Therefore, there is a need for CES treatments that address at least some of the problems associated with conventional CES treatments.

SUMMARY OF THE INVENTION

The present invention provides for applying one or more electric impulse trains to a patient. A generator is configured to generate at least one electric impulse train. The generator is further configured to vary the time period between the one or more electric impulse trains. There is an output for two or more electrodes. The electrodes are employable to convey voltages associated with the one or more impulse trains to the patient.

BRIEF DESCRIPTION OF THE DRAWINGS

For a more complete understanding of the present invention, and the advantages thereof, reference is now made to the following description taken in conjunction with the accompanying drawings, in which:

FIG. 4 illustrates a waveform generator having a dither and period oscillator and also having other aspects.

DETAILED DESCRIPTION

In the following discussion, numerous specific details are set forth to provide a thorough understanding of the present invention. However, it will be understood by those skilled in the art that the present invention can be practiced by those skilled in the art following review of this description, without such specific details. In other instances, well-known elements have been illustrated in schematic or block diagram form in order not to obscure the present invention in unnecessary detail. Additionally, for the most part, details have been omitted inasmuch as such details are not considered necessary to obtain a complete understanding of the present invention, and are considered to be within the skills of persons of ordinary skill in the relevant art.

It is further noted that, unless indicated otherwise, all functions described herein are performed by a processor such as a computer or electronic data processor in accordance with code such as computer program code, software, and/or integrated circuits that are coded to perform such functions.

Figure 1:
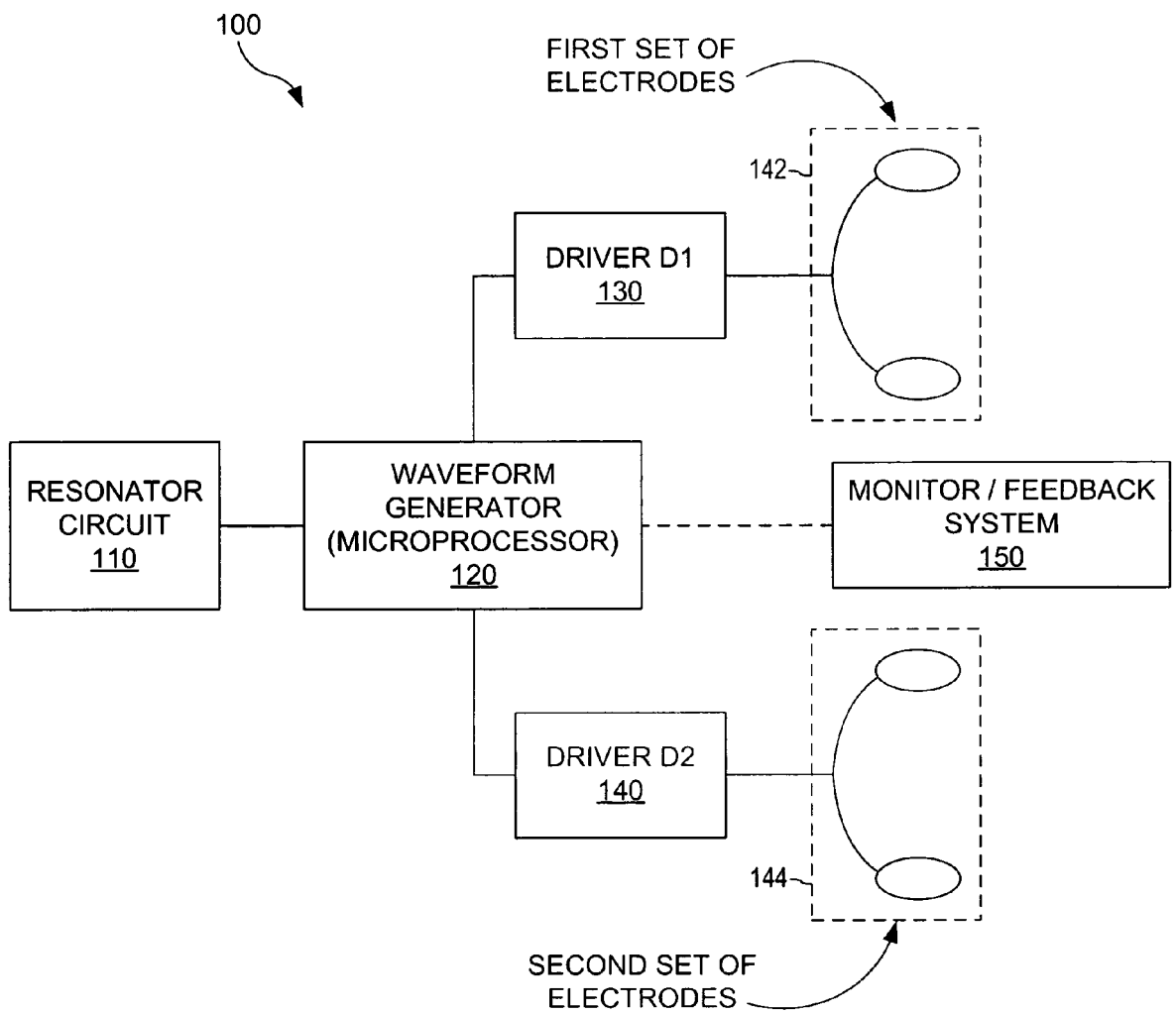
FIG. 1 illustrates a system for applying a dual pair of electrodes applying electric impulses with a dithered frequency and 180 degrees out of phase with one another.

Turning now to FIG. 1, illustrated is a system 100 for generating two pairs of electric impulse trains. Each pair of electric impulses, each impulse train having at least one of substantially equal applied positive or negative voltage, has the same period, but is out of phase with each other by 180 degrees. Then, the period between impulse trains is incrementally increased or decreased and regenerated, but the two newly generated electrical impulses are still 180 degrees out of phase with each other. U.S. Pat. No. 3,718,132 to Holt et al is hereby incorporated by reference in its entirety.

The system 100 provides a means of applying transcutaneous (external to the skin) electric current to the head. The micro-current stimulation is very small, less than 1.5 milliamperes and, although felt by the user, is self adjusted by the feedback system 150 to a comfortable level. Initial research indicates the system 100 can allow the user, especially those having dementia as in head injury, stroke and Alzheimer's disease, to potentiate memory recovery by facilitating additional blood flow/oxygen to those areas of the brain involved in the neurons/plasticity process. The system 100 can also normalize the Central Nervous System activity responsible for unbalanced sympathetic/parasympathetic efferent activity resulting from stress. It is well established that excessive or chronic stress can lead to heart attack, insomnia, anxiety, and depression and, among other problems, a weakening of the immune system.

The "dithered" output current slowly changes in frequency from 70 Hz to 110 Hz and back over a predetermined time period. This takes into account the normal differences in people. Each patient will receive stimulation at his/her optimum frequency as opposed to some who may not respond optimally at a "fixed" output frequency. The dithered feature can be stopped and set if the individual is shown to have a better response at one specific frequency in the range provided.

The system 100 has two substantially identical but separate driver circuits 130, 140 operating independently in the same system 100. One output connects bilaterally to the patient's head through adhesive type electrodes placed behind each ear. The other output is connected to the same type electrodes with one placed in the center of the forehead and the other at the nape of the neck just below the hairline.

In the system 100, a resonator circuit 110 is coupled to a waveform generator 120, such as a microprocessor. The waveform generator 120 is coupled to a driver D1 130 and a driver D2 140. Generally, the waveform generator 120 provides timing signals that ensure that the output of the two electrode outputs are always out-of-phase. Additionally, the waveform generator 120 allows the repetition rate of the pulses at the electrodes to be swept above, below and through a spectrum of fixed replication rates.

The driver D1 130 is coupled to a first set of electrodes 142. The driver D2 140 is coupled to a second set of electrodes 144. The resonator circuit 110 can comprise a crystal oscillator and one or more capacitors, employable to help ensure reliable timing. In one embodiment, the clock of the waveform generator 120 is controlled by a 4 MHz resonator circuit 110. This provides a very stable and accurate clock reference. Since the waveform generator 120 can execute one instruction every four clock cycles, software can generate timing signals by providing for a set of number of instructions between desired events.

The system 100 produces dithered pulse trains, having incremented or decremented periods between pulse trains. In one embodiment, the waveform generator 120 cycles 70 to 110 times per second for each set of electrodes 142, 144, a waveform of alternating current instead of a single current pulse. Because the alternating current sends bipolar current between the electrodes instead of unidirectionally, as would be the case with direct current, there is a net cellular polarization of zero to the patient during its use. This is considered a safety factor of major importance to the patient if the unit is to be used repeatedly and over a period of time, which it typically is.

In the system 100, the first set of electrodes 142 could be attached to the posterior and anterior portions of a test skull, and the second set of electrodes 144 could be attached to the left and right portions of a test skull. Use of the two sets of the electrodes can increase the area of the brain in which the current flows, as the current flows in the path of least resistance, and two different pathways can lead to a greater area of the brain being stimulated. Alternatively, other areas of the body can be stimulated by at least one set of the pairs of electrodes.

One advantage of the "dither" approach to incrementally increasing and decreasing the period between pulses is that different brains have differing responses to the same impulses. Therefore, use of the dithered periods between impulse trains allows for a greater probability of a given response being generated with the subject neurological tissue.

The system 100 can contribute to the solution of at least five important health problems: stress, inattention to task (that is, attention deficit), sleep deprivation, substance addiction, and brain plasticity. The system 100 provides an instrument and a therapeutic method that stimulates brain wave activity and thereby reduces the negative effects of stress, for example, depressed immune system, fosters longer attention to task, induces more restful sleep, reduces cravings for addictive substances; and improves brain plasticity.

In a further embodiment, a monitor/feedback system 150 is coupled to the waveform generator 120. The monitor 150 can be used to review blood flow within the brain, or other various indicia of effectiveness, as the period changes between the electrical impulse trains. Therefore, when the feedback system 150 shows a desired amount of blood flow or other stimuli, the monitor system 150 also notes the period of time between impulse trains. Therefore, as patients can have different responses to the same dither period, the more advantageous dither periods for different patients can be selected. In one embodiment, the monitor/feedback system 150 comprises a functional magnetic resonance imaging (MRI) system.

In a further embodiment, heart rate is monitored and used as a data point to calculate the period between impulse trains through a heart data rate monitor, which could be incorporated within the feedback system 150. Either a battery source can be used, or alternating current can be input into a converter and converted into direct current. Any readouts could be read out on the monitor/feedback system 150. The current applied through the drivers D1 and D2 could be altered to induce various states of sleepfullness or wakefulness, and so on. In a further embodiment, the measurement of the heart rate comprises measuring heart rate variability.

The system 100 could also be used to positively alter heart rate variability. As is understood by those of skill in the art, an erratic heart-beat can indicate the sympathetic and parasympathetic nervous systems out of balance. Through the application of the dithered impulse trains, the heart rate may be returned to a more stable and steady rhythm.

Verification of the various dither timing and out of phase timing of the system 100 is generally dependent on the embedded software (firmware) within the waveform generator 120, the driver D1 130 and the driver D2, 140 and on the resonator circuit 110. The resonator circuit 110 contains a piezoelectric crystal which is very precise at a given temperature. The firmware is programmed into each unit from a common file. Once programmed, the firmware is read back and compared to the original. A checksum further ensures no mistakes have been introduced.

In a further embodiment, the second set of electrodes 144 can be coupled to elsewhere other than the brain region. For instance, while the first set of electrodes 142 could still be coupled to the patient's skull, for instance, one electrode behind each ear, the second set of electrodes could be coupled to the back of the patient. One such area could have a set of electrodes placed between the shoulder blades of the patient.

Figure 2A:
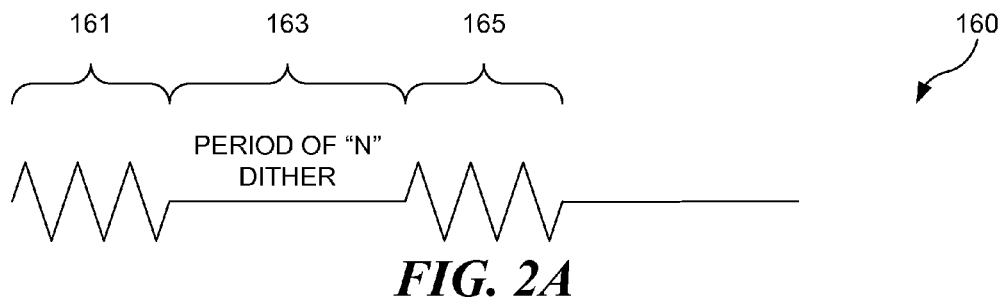
FIGS. 2A and 2B illustrates a first dithered pair of waves 180 degrees out of phase with one another.

Turning now to FIG. 2A, illustrated is a first waveform 160. An impulse train 161 is generated by a driver D1 130 and applied to the first set of electrodes 142. During a dither time 163, no electrical impulse is generated by the driver D1 130. Then, a second impulse train 165 is generated by the driver D1 130.

Figure 2B:
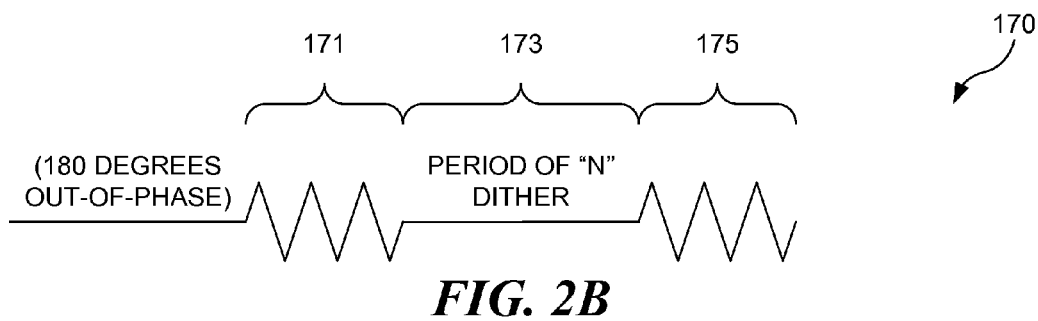

Turning now to FIG. 2B, the impulse trains 171, 175 of the waveform 170 generated by the driver D2 140 are 180 degrees (π) out of phase with the impulse trains 161 and 165 of the waveform 160, however, but the period of the "N" dither 163, 173 is the same for both drivers at this time.

Figure 2C:
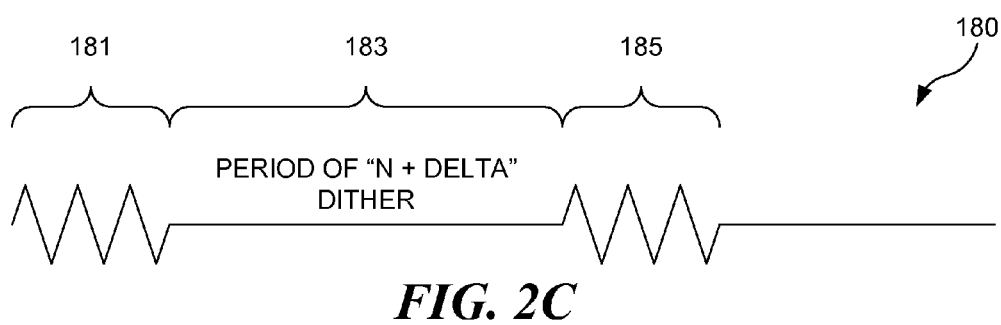
FIGS. 2C and 2D illustrate a second dithered pair of waves 180 degrees out of phase with one another.

Turning now to FIG. 2C, illustrated is a second dither period, N plus delta 183 of a waveform 180 at a different time than the generation of the period "N" dither of waveforms 160, 170. The impulse trains 181, 185, however, in this illustration, have substantially similar properties as the waveforms 161, 165, 171, and 175. The impulse trains 181, 185 are generated by the driver D1 130.

Figure 2D:
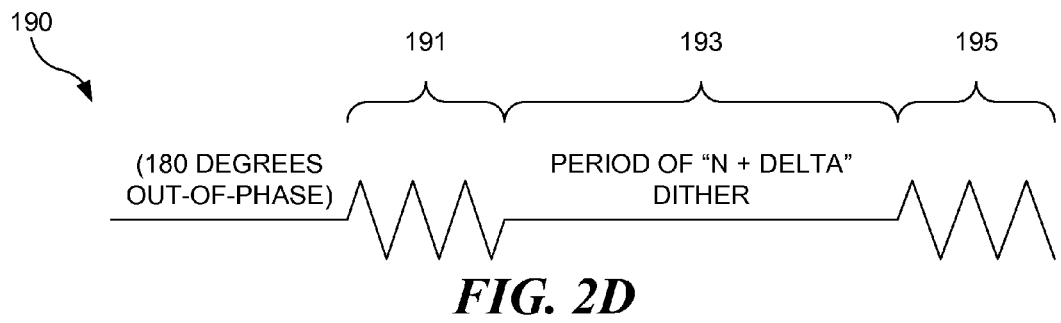

Turning now to FIG. 2D, the impulse trains 191, 195 of the waveform 190 generated by the driver D2 140 have substantially similar properties to impulse trains 181 and 185, and are also 180 degrees out of phase with impulse trains 181, 185. However, the period of time 193 between impulse trains 191, 195 is substantially similar to the period of time 183 between impulse trains 181, 185. Furthermore, the impulse trains 191, 195 and the impulse trains 181, 185 are substantially 180 degrees out of phase with one another.

Figure 3:
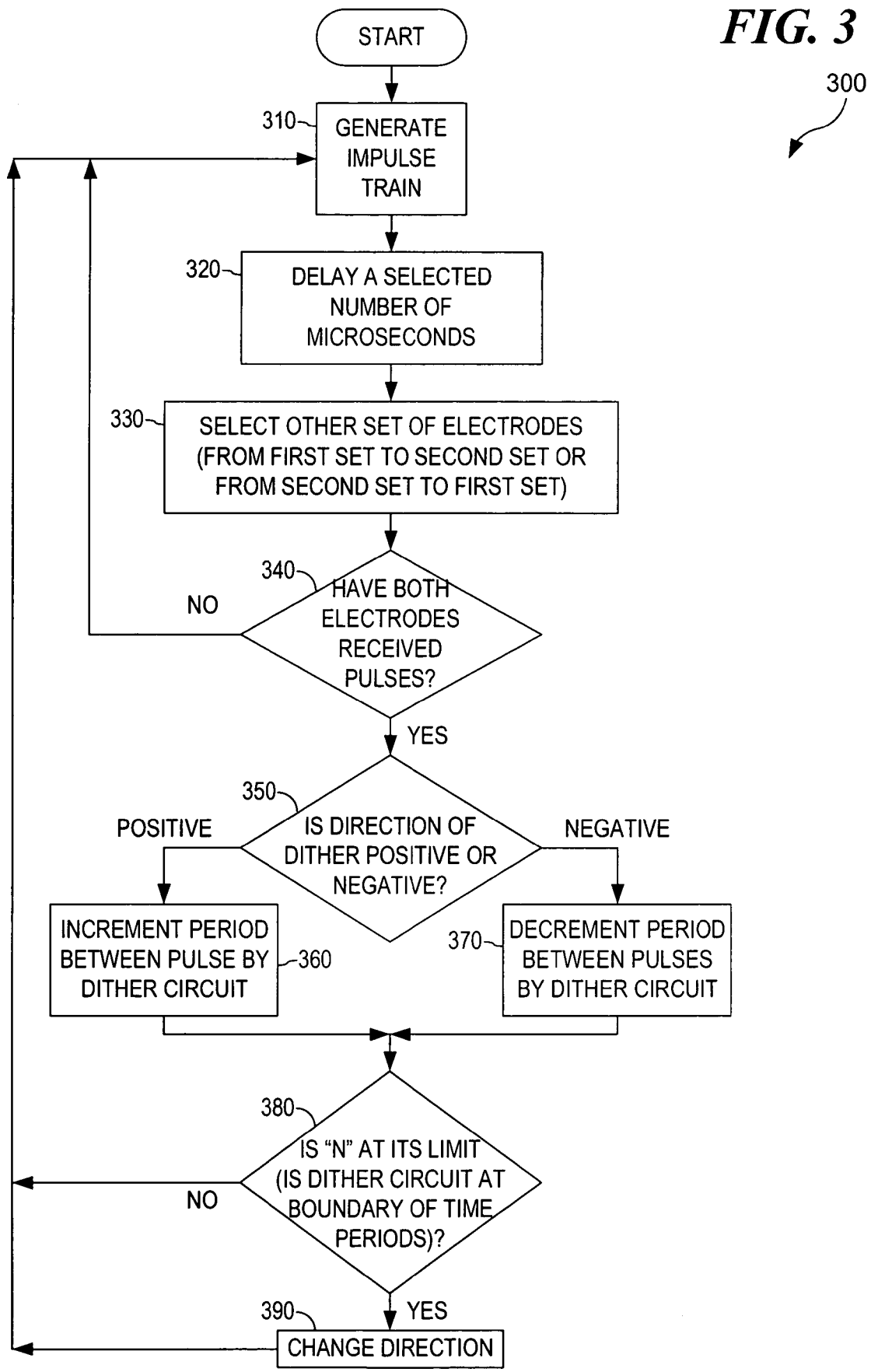
FIG. 3 illustrates a method of generating a dithered pair of electric impulses.

Turning now to FIG. 3, illustrated is a method 300 for varying the dither period between impulse trains as generated by the waveform generator 120. After a start step, a pulse train is generated in step 310 and applied to either the first set of electrodes 142 or the second set of electrodes 144, as appropriate. In step 320, a dither of a selected amount of time, such as a number of microseconds, is performed. In step 330, the other set of electrodes is selected by the waveform generator 120. In step 340, it is determined whether both electrode pairs 142, 144 have received pulses at the dither rate selected by the waveform generator 120. If both electrode pairs have not received pulses at the selected dither rate, then step 310 re-executes. b1

However, if both electrode pairs have received pulse at the selected dither rate, it is then determined in step 350 whether the direction of the dither is in the positive or negative direction. If the direction of the dither is in the positive direction, then in step 360, the period between impulses is incremented by a ditherer, such as a dither circuit. If the direction of the dither is in the negative direction, then in step 370, the period between impulses is decremented by a ditherer, such as a dither circuit. In step 380, it is determined whether the ditherer is at either of two predefined boundaries, either upper or lower, for the dither period. If the ditherer is not at either of two predefined boundaries, then step 310 re-executes. However, if the ditherer is at either of two predefined boundaries, then in step 390, the ditherer changes the direction, that is, increases if previously decreasing or decreases if previously increasing the dithering.

Turning now to FIG. 4, illustrated is a waveform generator 400. The waveform generator 400 has a battery save circuit/power off timer 420, a placebo on/off switch 430, and a dither/period oscillator 440.

Generally, the battery save circuit/power off timer 420 can be used to turn off the power to drivers 130, 140 if the system 100 has been generating dithered impulse trains for a set period of time, such as an hour, thereby reducing heat generation. This can also act as a safety feature for the patient.

Generally, the placebo on/off switch 430 can be used as a control for determining whether the subject believes that use of the device, on or off, is affecting him/her. For instance, a subject could believe that the system 100 has an effect when "on", but does not have an affect when "off". Therefore, the placebo switch can be used in both the on and off position, and the patient could believe that differing impulse trains are being applied, or even a complete lack of impulse trains. Therefore, the patients' outward symptoms could be studied and compared to his or her subjective belief.

The dither/period circuit 440 is used by the drivers 130, 140 to drive the first and second set of electrodes 142, 144. This circuit can generate waveforms as illustrated in FIGS. 2A-2D.

It is understood that the present invention can take many forms and embodiments. Accordingly, several variations can be made in the foregoing without departing from the spirit or the scope of the invention.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention can be employed without a corresponding use of the other features. Many such variations and modifications can be considered obvious and desirable by those skilled in the art based upon a review of the foregoing description of preferred embodiments. Accordingly, it is appropriate that the appended claims be construed broadly and in a manner consistent with the scope of the invention.

What is claimed is:

1. An apparatus for applying one or more electric impulse trains to a patient to stimulate at least one internal organ of the patient, comprising:
   a generator, wherein the generator is configured to generate two or more sets of electric impulse trains, and wherein the generator is further configured to vary a time period between the generation within each set of the electric impulse trains, wherein the time period is incremented or decremented in response to a boundary limit, and wherein a first set of the electric impulse trains is substantially 180 degrees out of phase with a second set of the electric impulse trains; and
   an output from the generator for each of the two or more sets of electric impulse trains, wherein the output of the two or more sets of electrodes changes in frequency within a range of about 70 Hz to about 110 Hz; and
   two or more sets of electrodes, a first set of the sets of electrodes employable to convey voltage associated with the first set of the impulse trains to the patient, and a second set of the sets of electrodes employable to convey voltage associated with the second set of the impulse trains to the patient.

2. The apparatus of claim 1, wherein the generator comprises a ditherer.

3. The apparatus of claim 2, further comprising a resonator circuit coupled to the ditherer.

4. The apparatus of claim 2, further comprising a placebo switch coupled to the ditherer.

5. The apparatus of claim 1, further comprising a feedback monitor coupled to the apparatus.

6. The apparatus of claim 5, wherein the feedback monitor comprises functional magnetic resonance imaging.

7. The apparatus of claim 1, further comprising a power off timer configured to disable at least a portion of the generator after a specified amount of time has passed.

8. The apparatus of claim 1, wherein an impulse train comprises at least one positive voltage pulse and a corresponding number of negative voltage pulses.

9. The method of claim 1, wherein the output of the two or more sets of electrodes changes in frequency within a range of 70 Hz to 110 Hz.

10. The method of claim 1, wherein the voltage is conveyed transcutaneously.

11. An apparatus for applying one or more electric impulse trains to a patient to stimulate at least one internal organ of the patient, comprising:
 a generator, wherein the generator is configured to generate two or more sets of electric impulse trains, wherein the generator is further configured to vary a time period between the generation within each set of the electric impulse trains, wherein the time period is incremented or decremented in response to a boundary limit; and
 an output from the generator for each of the two or more sets of electric impulse trains, wherein the output of the two or more sets of electrodes changes in frequency within a range of about 70 Hz to about 110 Hz; and
 the two or more sets of impulse trains corresponding to each of two or more sets of electrodes, a first set of the sets of electrodes employable to convey voltage associated with the first set of the impulse trains to the patient, and a second set of the sets of electrodes employable to convey voltage associated with the second set of the impulse trains to the patient.

12. The apparatus of claim 11, wherein the generator is further configured to a select a maximum time period between impulse trains of the same set.

13. The apparatus of claim 11, wherein the generator is further configured to select minimum time period separating a plurality of impulse trains.

14. The apparatus of claim 11, wherein the generator further comprises a ditherer configured to increase the time period separating a plurality of impulse trains.

15. The apparatus of claim 11, wherein a ditherer is configured to decrease the time period separating a plurality of impulse trains.

16. The apparatus of claim 11, further comprising an input of a first electrode coupled to a first driver, the first driver further coupled to the generator.

17. The apparatus of claim 11, further comprising an input of a second electrode of coupled to a second driver, the second driver further coupled to the generator.

18. The apparatus of claim 11, wherein a first impulse train and a second impulse train are out of phase with each other.

19. The apparatus of claim 18, wherein the first and second impulse trains are substantially 180 degrees out of phase with each other.

20. A method for generating a signal comprising automatically varying a period between a plurality of impulse trains employable for stimulating at least one internal organ of a patient, the method comprising:
 providing at least a first and second set of electrodes;
 generating an impulse train on at least the first set of electrodes;
 delaying a selected number of microseconds as a function of a dither period;
 following the delay, determining if the first and the second set of electrodes have received impulse trains;
 if both sets of electrodes have not received impulse trains, generating an impulse train on the second set of electrodes;
 determining if a direction of dither is positive or negative;
 if the direction is positive, incrementing the period between the plurality of impulse trains;
 if the direction is negative, decrementing the period between the plurality of impulse trains; and
 determining if the incremented or decremented period has reached a boundary limit.

21. The method of claim 20, flirt her comprising determining whether the period is at either an upper limit or a lower limit.

22. The method of claim 21, wherein if the period is at a limit, changing the direction of the dither.

23. The method of claim 21, wherein both sets of electrodes are coupled to the head of a patient.

24. The method of claim 20, wherein one electrode is coupled to the head of a patient and the second electrode is coupled elsewhere on the patient.

25. The method of claim 20, wherein the second electrode is coupled between the shoulder blades of the patient.

26. The method of claim 20, further comprising monitoring a heartbeat and correlating the heartbeat to the period between the plurality of impulse trains.

27. The method of claim 26, wherein monitoring a heartbeat further comprises monitoring heart rate variability.

28. The method of claim 20, further comprising determining a response of a patient as a function of the period between the plurality of impulse trains.

29. The method of claim 20, wherein the time period between impulse trains comprises a plurality of microseconds.

* * * * *